US008506981B1

(12) United States Patent
Borden

(10) Patent No.: US 8,506,981 B1
(45) Date of Patent: Aug. 13, 2013

(54) COMPOSITIONS AND THEIR USE IN BONE HEALING

(71) Applicant: Synergy Biomedical LLC, Phoenixville, PA (US)

(72) Inventor: Mark D. Borden, Collegeville, PA (US)

(73) Assignee: Synergy Biomedical LLP, Collegeville, PA (US)

( * ) Notice: Subject to any disclaimer, the term of this patent is extended or adjusted under 35 U.S.C. 154(b) by 0 days.

(21) Appl. No.: 13/868,388

(22) Filed: Apr. 23, 2013

Related U.S. Application Data

(63) Continuation of application No. 13/659,095, filed on Oct. 24, 2012.

(60) Provisional application No. 61/550,706, filed on Oct. 24, 2011.

(51) Int. Cl.
*A61F 2/00* (2006.01)
*A61K 9/64* (2006.01)
*A61K 9/52* (2006.01)
*A61K 9/54* (2006.01)
*A61K 9/50* (2006.01)
*A61K 9/16* (2006.01)

(52) U.S. Cl.
USPC .......... 424/422; 424/423; 424/426; 424/456; 424/457; 424/458; 424/489; 424/490; 424/497; 514/17.2; 501/11; 106/35; 433/215; 433/217.1; 433/226; 433/228.1; 623/16.11

(58) Field of Classification Search
None
See application file for complete search history.

(56) References Cited

U.S. PATENT DOCUMENTS

| 4,775,646 | A | * | 10/1988 | Hench et al. ............... 501/2 |
| 4,851,046 | A | | 7/1989 | Low et al. |
| 5,204,106 | A | | 4/1993 | Schepers et al. |
| 5,658,332 | A | | 8/1997 | Ducheyne et al. |
| 6,054,400 | A | | 4/2000 | Brink et al. |
| 6,228,386 | B1 | | 5/2001 | Yang |
| 6,248,344 | B1 | | 6/2001 | Ylanen et al. |
| 7,329,126 | B2 | | 2/2008 | Cook et al. |
| 2006/0067969 | A1 | * | 3/2006 | Lu et al. ............... 424/423 |
| 2010/0247478 | A1 | * | 9/2010 | Clineff et al. ............... 424/78.32 |
| 2011/0150963 | A1 | | 6/2011 | Clineff et al. |
| 2011/0243913 | A1 | * | 10/2011 | Antonio ............... 424/94.5 |

FOREIGN PATENT DOCUMENTS

EP 2322134 5/2011
WO WO 2011/088157 7/2011

OTHER PUBLICATIONS

Sepulveda et al., Key Engineering Materials vols. 192-195 (2001); pp. 629-634.*
NPL search string in Google Scholar; 2 pages; downladed Jun. 12, 2013.*
NPL search string in Google; 2 pages; downladed Jun. 12, 2013.*
Bosetti et al., "The Effect of Bioactive Glasses on Bone Marrow Stromal Cell Differentiation", Biomaterials, Jun. 2005, 26(18), 3873-3879.
Hench et al., "Bonding Mechanism at the Interface of Ceramic Prosthetic Materials", J. Biomed. Mater. Res. Symposium, 1971, 2, 117-141.

(Continued)

*Primary Examiner* — Robert A Wax
*Assistant Examiner* — Jeffrey T Palenik
(74) *Attorney, Agent, or Firm* — Woodcock Washburn, LLP

(57) ABSTRACT

The present invention is directed to implantable compositions comprising substantially spherical bioactive glass particles.

17 Claims, 11 Drawing Sheets

(56) References Cited

OTHER PUBLICATIONS

Hench et al., Biological Applications of Bioactive Glasses, Life Chem. Rep., vol. 13: 187, 1996, 187-241.
Jell et al., "Gene Activation by Bioactive Glasses", J. Mater. Sci.: Mater. Med., Feb. 2006, 17, 997-1002.
Kokubo et al., "Solutions able to Reproduce in vivo surface-structure changes in bioactive glass-ceramic", J. Biomed. Mater. Res., 1990, 24, 721-734.
Oonishi et al., "Particulate Bioglass Compared with Hydroxyapatite as a Bone Graft Substitute", Clinical Orthopaedics and Related Research, Jan. 1997, 334, 316-325.
Xynos et al., "Ionic Products of Bioactive Glass Dissolution Increase Proliferation of Human Osteoblasts and induce Insulin-like growth factor II mRNA Expression and Protein Synthesis", Biochem. Biophys. Res. Commun., Sep. 2000, 276(2), 461-465.
Jillavenkatesa et al., "Particle Size Characterization", NIST Recommended Practice Guide, Jan. 2001, 167 pages.

\* cited by examiner

| Bioactive Glass Particle Type | 6 Week MicroCT | 12 Week MicroCT |
|---|---|---|
| 32-710um Irregular Particles | | |
| 90-180um substantially spherical particles | | |
| 180-355um substantially spherical particles | | |
| 355-500um substantially spherical particles | | |
| 90-180/355-500um substantially spherical particles | | |
| 180-355/355-500um substantially spherical particles | | |

FIGURE 9

COMPOSITIONS AND THEIR USE IN BONE HEALING

CROSS REFERENCE TO RELATED APPLICATIONS

This application is a continuation of U.S. application Ser. No. 13/659,095, filed Oct. 24, 2012, which claims the benefit of U.S. Provisional Application No. 61/550,706, filed Oct. 24, 2011, the entireties of which are incorporated herein by reference.

TECHNICAL FIELD

The invention is directed to the use of substantially spherical bioactive glass particles in materials useful for bone healing.

BACKGROUND

Bioactive glasses are well known surgical materials that have been used as bone graft materials for over 24 years. The original 45S5 bioactive glass composition was discovered by Hench and has the following composition: 45% $SiO_2$, 24.5% $Na_2O$, 24.5% CaO and 6% $P_2O_5$ [Hench J. Biomed. Mater. Res. Symp. 117-141 (1971)]. As a bone graft material, bioactive glasses have the unique property of forming a hydroxy-carbano-apatite (HCA) layer on the glass surface when implanted in vivo. The formation of this layer is linked to the glass dissolution, subsequent release of calcium (Ca) and phosphorus (P) ions, and the formation of a Ca—P rich layer on the glass surface. The layer eventually crystallizes into hydroxy-carbano-apatite and results in an interfacial bond between the bioactive glass and the bone which improves bone healing around the bioactive glass particles.

Following the Hench's original discovery of the 45S5 formula, additional compositions were evaluated but it was found that only a narrow range of the CaO—$SiO_2$—$Na_2O$ ratio was bioactive with the 45S5 composition providing the best results. Hench et al Life Chem Rep 13: 187 (1996).

Work was also conducted on determining an optimal particle size. Initially, this was focused on improving intraoperative handling of the wet glass during surgery. Low et al. (U.S. Pat. No. 4,851,046) examined the effect of 45S5 bioactive glass particle size on the intraoperative cohesiveness and manipulation of the glass. Testing showed that a broad 90-710 μm particle size had the best intraoperative handling and in vivo bone formation in a primate periodontal defect.

Schepers and Ducheyne (U.S. Pat. No. 5,204,106) also examined the effects of 45S5 bioactive glass particle size. This was done to control the disintegration and dissolution rate of the bioactive glass particles. It was shown that the implantation of various particle sizes in the canine jaw bone resulted in different biological responses to the glass. The results showed that the 280-425 μm size range provided the best bone formation response at this skeletal site.

Although the results from the prior jaw bone study found sub-optimal responses for smaller particles, this was attributed to the higher fluid flow and vascularity in the jaw. This led to faster resorption of the glass before sufficient bone growth could occur. The appendicular skeleton, however, has lower vascularity and minimal fluid flow as compared to the jaw. Following their original dental study, Schepers and Ducheyne (U.S. Pat. No. 5,658,332) found that smaller particles (200-300 μm) of bioactive glass implanted in the appendicular skeleton did not resorb at the fast rate seen in the jaw. They found that the smaller size range increased the bone formation rate by providing a nuclei for bone tissue formation. Testing conducted in a rabbit iliac crest defect showed that the 200-300 μm particle size supported bone growth on the surface of the particles (osteoconduction) and within the central area of the particles (excavation). Additionally, in vivo testing of various glass compositions showed that the 45S5 glass had the best bone formation.

Further work by Yang (U.S. Pat. No. 6,228,386) addressed the cost issue related to manufacturing narrow ranges of bioactive glass. Yang's work expanded Schepers and Ducheyne's 200-300 μm to 200-400 μm in order to reduce the manufacturing cost of the bioactive glass particles. This broader size range was tested in an in vivo rabbit iliac crest model and was compared against Schepers and Ducheyne's 200-300 μm range and the original 90-710 μm range disclosed by Low. Although the results were semi-quantitative and were based on 2 animals per group, the data did show that the slightly broader 200-400 μm had the best performance.

The prior art showed that particle size had effects on particulate intra-operative handling, glass dissolution, function as a bone nucleation site, and manufacturing costs. Following this initial work, it was discovered that a new characteristic of the glass was the main contributors to bioactive glass bone healing. In a study by Oonishi, 45S5 bioactive glass was compared directly against a widely used bone graft material (hydroxyapatite) in an in vivo rabbit femur model [Oonishi et al. Clin. Orthop. Rel. Res. 334:316-325 (1997)]. The results showed that the bioactive glass resulted in faster and more robust bone formation than hydroxyapatite. Oonishi hypothesized that the increased bone formation with 45S5 glass was attributed to the release of silica, calcium, and phosphorus ions which stimulated the colonization and proliferation of stem cells on the surface of the glass. This finding was later confirmed by several studies which showed that the ions released from bioactive glass increased bone formation through enhanced cellular differentiation, proliferation, and protein expression [Xynos et al. Biochem Biophys Res Commun 276: 461-465 (2000); Bosetti et al Biomaterials 26: 3873-3879 (2005); Jell et al. J. Mater. Sci: Mater. Med. 17:997-1002 (2006)].

Although the original bioactive glass optimization data evaluated the size of the glass particle, all of this work was based on using irregular glass particles and did not take into account the recent data showing that ion release has a significant impact on the ability of bioactive glass to promote bone healing. The irregularly-shaped particles of the prior art were sieved to specific size ranges and had a highly irregular and random shape with rough, jagged edges. In addition, the isolation of specific size ranges is not completely accurate due to oblong, "rice grain" shaped particles that may or may not pass through the sieve during the separation process.

The prior art has also shown that bioactive glass that is too small can quickly dissolve and lead to a burst release of ions to the site that could have a detrimental effect on bone healing (U.S. Pat. No. 5,658,332). Conversely, particles that are too large may release the ions too slowly and the bioactive glass would not benefit from the short-term ionic stimulation of local cells. Further, the teachings of the prior art indicate that it is essential to utilize irregular-shaped, rough-edged particles with microcracks in order to achieve a beneficial bone healing response.

Further optimization of bioactive glass particle shape and size to produce new materials is needed to further improve the bone-healing response.

SUMMARY

The invention is directed to compositions implantable into mammalian bodies comprising a physiologically acceptable carrier and substantially spherical bioactive glass particles. Also within the scope of the invention are substantially spherical bioactive glass particles having a bimodal particle size distribution. Pre-reacted, mechanically-stabilized particles are also within the scope of the invention. Sintered, substantially spherical bioactive glass particles are also described.

BRIEF DESCRIPTION OF THE DRAWINGS

FIG. 9 shows microCT images of 6 and 12 week rabbit femur study specimens from the substantially spherical 45S5 particles of the invention and the irregular particle group of the prior art. The particles of the invention showed increased bone formation in the center of the defect.

DETAILED DESCRIPTION OF ILLUSTRATIVE EMBODIMENTS

In contrast to the prior art's disclosure that irregular-shaped particles of bioactive glass are necessary for bone healing, it has now been unexpectedly discovered that the use of substantially spherical bioactive glass particles, in particular, 45S5 glass particles, significantly improves the rate of bone formation, bone fusion, and bone healing. It has also now been discovered that the use of substantially spherical bioactive glass particles, having a particular unimodal or bimodal particle size range, even further improves the rate of bone formation, bone fusion, and bone healing. Such materials, and their use in biomaterials, for example bone repair implants, are described herein.

The materials of the invention can be used as implantable bone grafts in all areas of the skeleton including long bones, spine, craniomaxillofacial, dental, and periodontal bone. As used herein, "implantable" refers to physiologically acceptable materials that can be placed into a mammalian body. Such physiologically acceptable materials will be sterile, non-pyrogenic, and non-immunogenic. Mammals envisioned to be treated using the compositions and methods of the invention include humans and domesticated animals such as dogs, cats, and horses.

The present invention is directed to bone grafts made of a bioactive glass material, such as 45S5 bioactive glass, borate glass, or any other suitable bioactive glass material. Exemplary materials can comprise combinations of $SiO_2$ and $CaO$; $SiO_2$, $CaO$, and $P_2O_5$; or $SiO_2$, $CaO$, $P_2O_5$, and $Na_2O$. These materials, as well as other material not including the recited combinations, are well known in the art.

The materials of the invention comprise bioactive glass particles of a specific shape and size that result in greater biological activity and better bone formation than prior irregular shaped bioactive glass particles. Substantially spherical bioactive glass particles, having the particle size distributions described herein for use in the invention can be prepared according to methods known in the art and can be custom-made by manufacturers such as Mo-Sci Corporation (Rolla, Missouri).

One aspect of the present invention is to use bioactive glass particles that have the most uniform ion release profile. The bioactive glass particles used within the scope of the invention include particles that are "substantially spherical." As used herein, "substantially spherical" refers to particles having a substantially circular or oval cross-section and appearing as round to round-ish particles at the microscopic level, for example, in a scanning electron micrograph image. Particles that are oblate spheroids, that is, particles that are rotationally symmetrical ellipsoids with a polar axis shorter than the diameter of the equatorial circle whose plane bisects it, are also within the scope of the "substantially spherical" particles of the invention.

Figure 1:
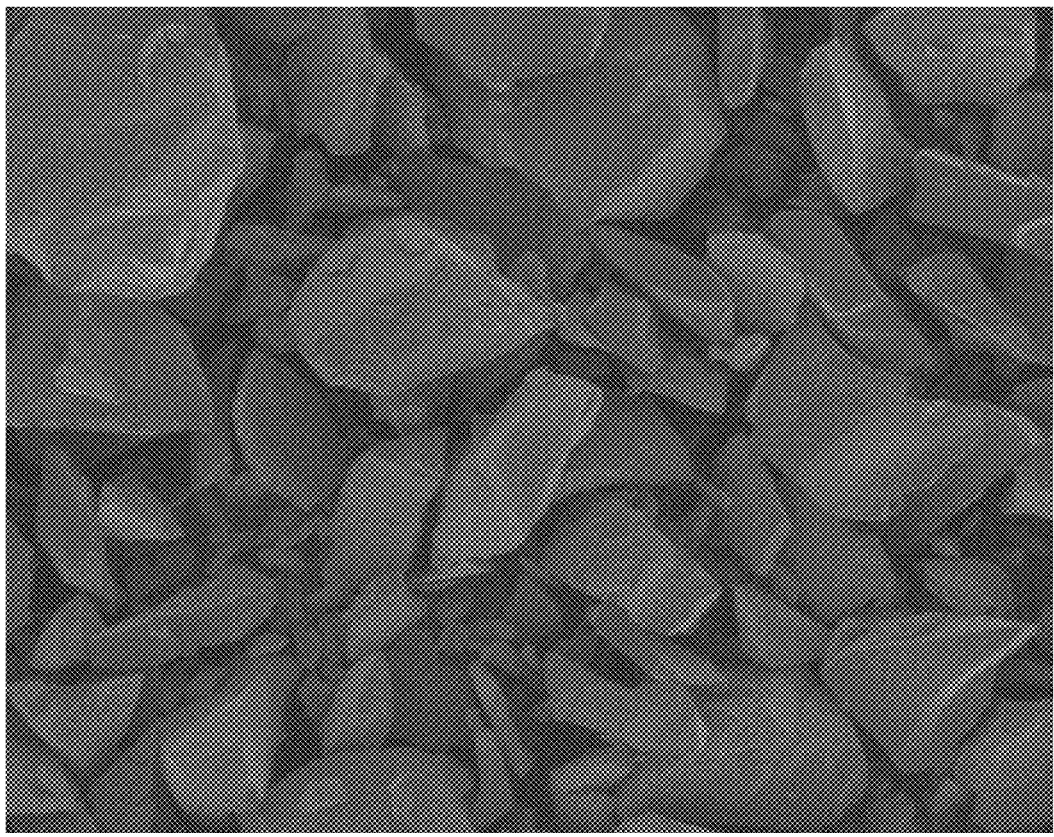
FIG. 1 depicts a scanning electron micrograph image of 45S5 particles of the prior art (32-710 µm).

Whether the particles are substantially spherical can be determined using methods known in the art. After manufacturing the particles, they are microscopically inspected to qualitatively evaluate whether the particles are substantially spherical. The substantially spherical bioactive glass particles of the invention are shaped in contrast to typical bioactive glass particles having an irregular shape and rough surface that is based on the shattering or grinding of the glass following melt formation (FIG. 1). Particles that have a rough surface, are oblong spheres with a tail, are broken spherical fragments, or are particles that are fused together are not considered substantially spherical within the scope of the invention.

The substantially spherical bioactive glass particles of the invention preferably incorporate a unimodal or bimodal particle size distribution. As used herein, "bimodal particle size distribution" refers to the materials of the invention wherein the majority of the particle sizes fall within the scope of two particle size distributions. A preferred embodiment of a bimodal distribution of the invention will comprise a minority of small particles and a majority of larger particles. Compositions of the invention comprising a bimodal particle size distribution may include a minority of particle sizes falling outside the scope of either of the two specified particle size distributions. Preferably, at least 60-99% of the particles, by weight, will fall within the two specified particle size distributions. More preferably, at least 80-90%, for example 85%, of the particles, by weight, will fall within the two specified particle size distributions.

Multimodal particle size distributions are also envisioned. In such multimodal distributions, a majority of the particles sizes falls within the scope of three or more particle size distributions.

In preferred embodiments, the materials of the invention will include substantially spherical bioactive glass particles having a first particle size distribution between 32 and 200 µm and a second particle size distribution of between 300 and 800 µm. Preferably, between 5% and 50% of the particles, more preferably about 10% of the particles, by weight, will have particle sizes falling within the 32 to 200 µm, more preferably within a 90 to 180 µm range.

Also preferred are embodiments having between 50% and 95% of the particles, more preferably about 90% of the particles, by weight, particles sizes falling within the 300 and 800 µm range, preferably 355 to 500 µm.

In particularly preferred embodiments, the materials of the invention will include substantially spherical bioactive glass particles having a first particle size distribution between 90 and 180 µm and a second particle size distribution of between 355 and 500 µm.

Throughout the present specification, the term "substantially spheroidal" has been used to define particles of bioactive glass which are preferred for use in the invention as compared to particles which are not preferred. It is to be understood that the defined term "substantially spherical" is a qualitative one and difficult to measure or determine through mechanical means. Accordingly, particles should be seen to be "substantially spherical" if they may be visualized via microscopy by a person of skill in the art to be generally spherical in overall three dimensional shape and to have a preponderantly smooth surface. It will be appreciated that few objects, either in nature or created by the hand of man, are truly, geometrically spherical. Rather, families of shapes approaching geometrical sphericality are considered to be spheres or substantially spherical. Thus, oblate spheroids, spheroids having one or more protuberances or bulges, and spheroids which include one or more dimples or depressions may, if seen to be overall approaching sphericality, be included in the set of "substantially spherical" particles.

Of equal importance to the overall geometrical shape is the smoothness of the particulate surface. In this regard, particles preferred for use in the present invention are to be distinguished from those taught by the prior art for use in bioactive glass in that such prior particles are at least preponderantly rough and fractured, not smooth. Smoothness, again, is a qualitative property of particles of the invention, which property is determined by visualization under microscopy by a person skilled in the art. It will be understood that the particles of the prior art are rough or fractured, having multiple angular or jagged formations upon them. Indeed, the prior art is believed to have intentionally caused fracturing and rough morphology in order to increase particle surface area. The present particles in the set of "substantially spherical" bioactive glass particles are not subjected to forces which are likely to result in such morphology; rather smoothness of the surface is desired.

Not all of the particles of bioactive glass used in the practice of one or more of the embodiments of the present invention need to be "substantially spherical." Within the scope of the invention, while the largest percentages by number of particles which are classified as "substantially spherical" are preferred, good results may be attained with the employment of particles which are at least about 70% by number of the particles which are both within the preferred size ranges and "substantially spherical." Still more preferred is employment of particles which are between 70% to about 90%, preferably about 80% or 85%, by number of the particles which are both within the preferred size ranges and "substantially spherical."

The bimodal particle size distribution of substantially spherical bioactive glass particles can be created by mixing, for example, by mechanical means, two particle size distributions of bioactive glass particles. Sieving techniques known in the art can be used to separate the substantially spherical particles into distinct size ranges. Such techniques are more accurate with the present invention because the particles have a more regular shape than those of the prior art. This allows for precise size ranges to be isolated using the particles of the invention.

Figure 4:
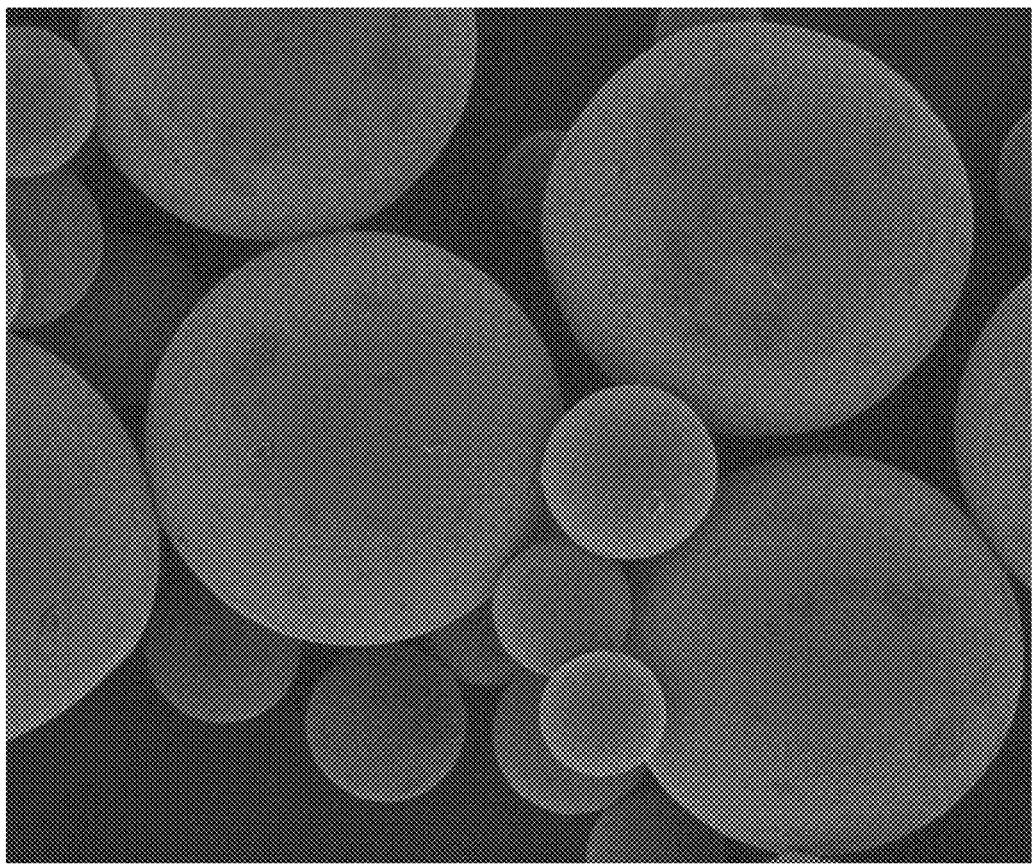
FIG. 4 shows a scanning electron micrograph image of a bimodal particle size range of one embodiment of the invention—substantially spherical 45S5 bioactive glass.

The sieving process allows for size range combinations of two or more sizes to be created. Sieving is a well known technique in the art and these techniques are described in, for example, NIST Recommended Practice Guide, Special Publication 960-1, Particle Size Characterization, January 2001. Using a combined size range, the release profile may be altered to provide an optimal release from particles of various sizes. An example of a bimodal size range containing two substantially spherical sizes is shown in FIG. 4. In this embodiment, a bioactive glass spherical mixture is formed by combining a percentage, preferably a low percentage, of small, substantially spherical bioactive glass particles with a percentage, preferable a greater percentage, of larger, substantially spherical bioactive glass particles.

In the materials of the invention, smaller particles provide an initial controlled release of ions to stimulate the healing process. Since the ion release from these particles is moderated by the compositions described herein, it can be controlled to prevent the detrimental release of an excessive amount of bioactive glass ions. Additionally, the presence of larger particles allows the particles to act as a scaffold for continued bone formation. These particles have a slower dissolution and resorption rate and will be able to function as an osteoconductive surface throughout the healing process.

Figure 2:
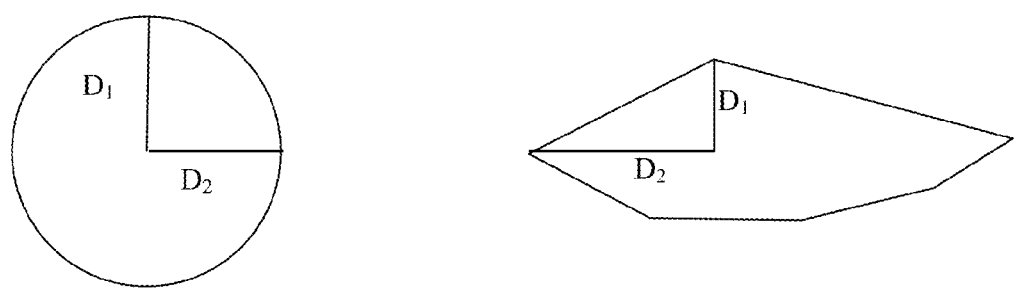
FIG. 2 shows a comparison of a uniform sphere with an equal radius (D1=D2) vs an irregular particle of the prior art with an unequal radius (D1≠D2).

The bioactive glass particles of the invention use the shape having the most reproducible ion release and optimal 3-dimensional packing. In examining various geometric shapes, the spherical form was chosen due to the generally consistent distance from the center of the particle to the edge, the round, generally uniform surface, and the ability to form a completely interconnected porosity due to its 3-dimensional packing (FIG. 2). A substantially spherical bioactive glass particle provides the most consistent particle geometry and a controllable ion release profile.

Figure 3:
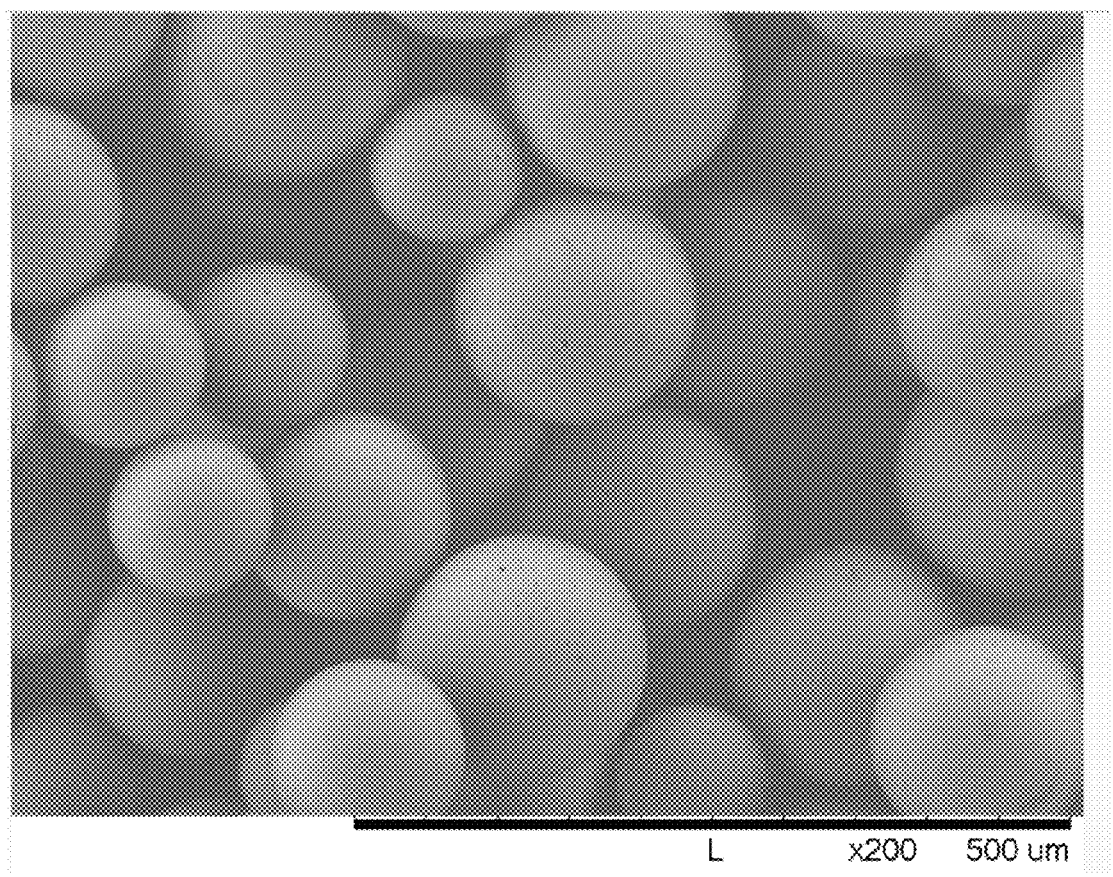
FIG. 3 shows a scanning electron micrograph image of substantially spherical 45S5 particles of the invention.

An example of substantially spherical 45S5 bioactive glass particles is shown in FIG. 3. When implanted in vivo, the exposure of the bioactive glass to body fluid initiates a dissolution process that releases ions out of the glass. Since the dissolution process is dependent on the particle shape, the use of a uniform spherical particle provides controlled ion release. By changing the particle size, the resultant ion release profile can also be changed. Dissolution testing has shown that smaller particles provide quicker release while larger particle provide slower release.

Another advantage of using spherical particles is that the packing of the particles in 3-dimensional space is more conducive for bone in-growth than the porosity created from the packing of irregular particles. Packing of the substantially spherical particles results in a completely interconnected porosity with open pores and no pore blockages. Pore size control is achieved by using particles of a specific diameters (larger spheres create larger pores).

Figure 5:
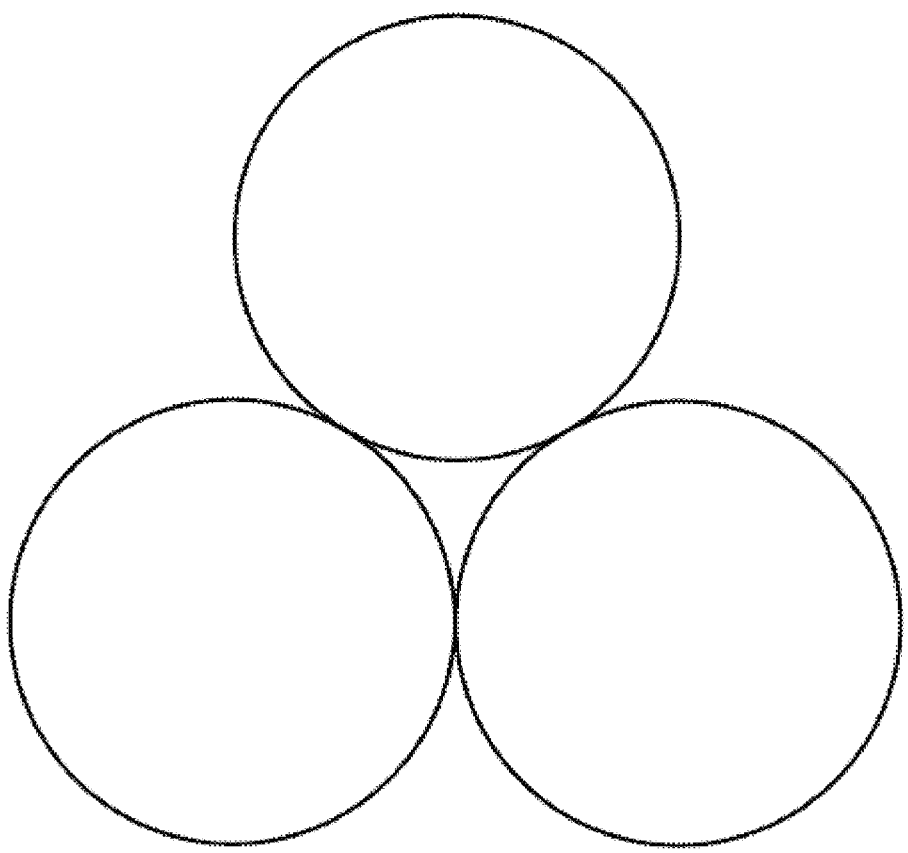
FIG. 5 shows the packing of three spheres resulting in a triangular shaped pore.

It has been previously shown that bone in-growth into porous structures is dependent on pore size [Hollis et al. Encyclopedic Handbook of Biomaterials and Bioengineering Boca Raton: CRC Press pp. 806-807 (1995)]. Pores that are too small will not allow bone in-growth into the porous structure while pores that are too large will slow down the bone formation process. An advantage to sphere packing is that pore size can be controlled by the size of the particle. In addition, the rounded surface of the substantially spherical particles prevents the particles from packing in an arrangement that would prevent the formation of porosity or an arrangement that results in pores too small for bone in-growth. In sphere packing, the smallest pore that can be created occurs from the packing of three particles together (FIG. 5). By utilizing a larger sphere, pores that are too small for bone in-growth can be avoided. As a result, the substantially spherical particles of the present invention can create a pore system that is completely interconnected and allows bone growth throughout the entire porosity.

Figure 6:
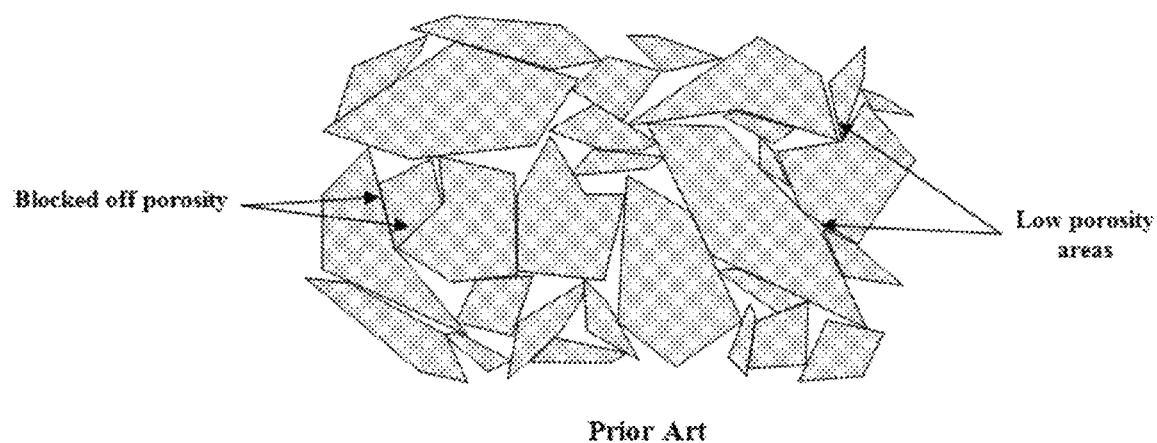
FIG. 6 shows the denser packing of irregular particles of the prior art indicating areas of blocked porosity and low porosity.

Conversely, irregular shaped particles can pack into denser arrangements with a lower % porosity, smaller pores, and areas of "blocked off" porosity. In particular, the flat surface and small aspect ratio of irregular particles allows for packing that creates areas of little to no porosity (as shown in FIG. 6). This type of dense packing would reduce the amount of bone that could form between the particles and within the implant site.

Also within the scope of the invention are methods for improving the bioactivity of bioactive glass particles. This aspect of the invention can be applied to all forms of bioactive glasses including irregularly-shaped particles, regularly-shaped particles, spherical particles, fibers, and porous scaffolds. In this embodiment of the invention, the bioactive glass is incubated in an ionic solution such as simulated body fluid (SBF) during the manufacturing process to initiate the formation of a layer of hydroxy-carbano-apatite (HCA) on the glass surface. When implanted in vivo, the presence of the HCA layer will provide a better surface for the attachment and formation of new bone. Additionally, if the HCA layer is already present at the time of implantation, the healing response would be accelerated by eliminating the time needed to form the layer in vivo. This would allow for faster bone formation immediately following implantation.

Figure 7:
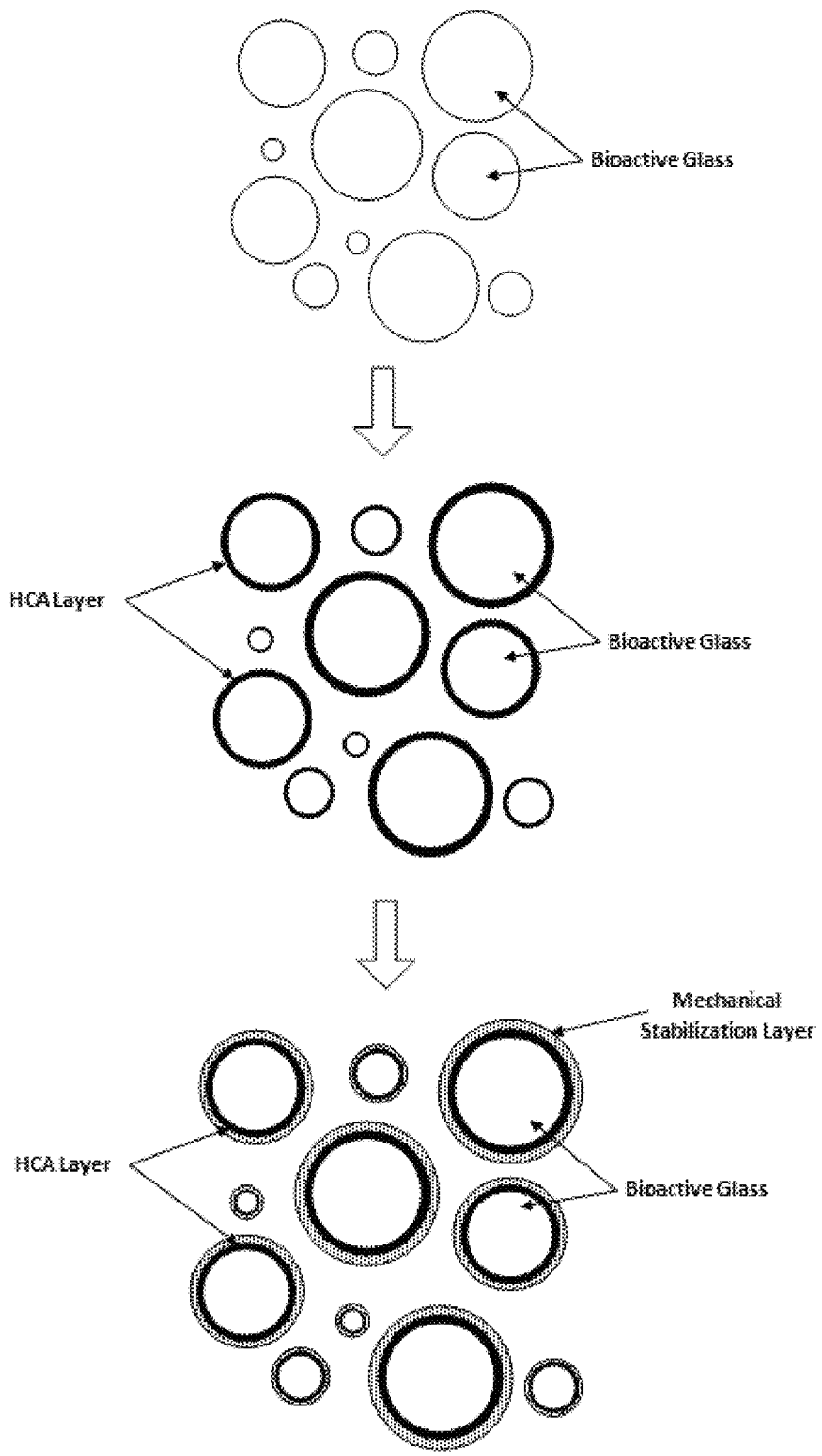
FIG. 7 shows the formation of an HCA layer on the surface of a bioactive glass particle followed by outer coating with a mechanical stabilization layer.

Although a pre-formed HCA layer would be advantageous to bone healing, the layer formed using an in vitro process is brittle and is easily detached from the surface of the bioactive glass. Normal handling during manufacturing and distribution would remove the pre-reacted HCA surface layer and the glass would lose this advantageous coating. To circumvent this issue, the HCA layer on the bioactive glass can be mechanically stabilized by the addition of an outer coating (FIG. 7). This outer coating can include water-soluble, bioresorbable materials such as hyaluronic acid, gelatin, alginate, chitosan, or other hydrogels, as well as mixtures thereof. In these embodiments, the bioactive glass is incubated in an ionic solution such as SBF and the HCA layer is allowed to form. Once the surface is substantially coated with HCA, the bioactive glass can be immersed in a separate outer coating solution which is allowed to dry on the glass surface. Following this process, the outer coating will tend to stabilize the HCA layer, reduce its brittleness, and prevent it from becoming detached during normal handling and processing. When the mechanically stabilized, HCA-coated bioactive glass particles of the invention are placed in a bone defect, the outer coating will dissolve and expose the HCA layer to the surrounding fluid and cells and allow bone healing to start.

Also within the scope of the invention is the use of the substantially spherical bioactive glass particles of the invention in bone graft or cement materials. One exemplary embodiment of the present invention is a composition that is a bone grafting "putty" that comprises the substantially spherical bioactive glass particles of the invention in combination with a physiologically acceptable carrier to form the bone grafting putty. As used within herein, a "putty" is a composition having a soft, moldable, paste-like consistency. The bone grafting putty can be made by mixing the bioactive glass particles of the invention into a moldable, "doughy" composition to create a putty.

Since ion release is activated by an aqueous environment, water-based carriers cannot be used. Preferably, the physiologically acceptable carriers used herein are non-aqueous compounds that are non-pyrogenic, non-immunogenic, sterilizable, and have a short-term resorption profile. Preferably, the carriers used in the bone grafts of the invention will tend to dissolve in about 3-7 days either in vitro or in vivo.

Preferred carriers for use in the putties of the invention include one or more phospholipids, polyethers, or polyhydroxy compounds. Preferably, the carriers are an admixture of two or more components.

An advantage of a dual- or multi-component carrier is that it allows the properties of the carrier to be optimized to the bone graft application. For example, waxy-based polymers or phospholipids may not be suitable alone to create a moldable carrier. By mixing them with a liquid that functions as a softening agent, however, a moldable carrier can be created. Further, altering the concentration of the softening agent allows for a variety of putty carriers to be created. This includes a "paste-like" putty for adhering to other bone graft materials and the implant site, an extrudable putty that can be delivered by a syringe or cannula, and a firm putty to be used as a stand-alone bone graft.

Preferred carriers for use in the putties of the invention include admixtures of phospholipids, for example, phosphatidylcholines, with triglycerides, monoglycerides, fatty acids, or combinations thereof. Such materials are known in the art per se and are commercially available from suppliers such as Lipoid GmbH (Ludwigshafen, Germany) and American Lecithin Company (Oxford, CT).

In exemplary putty embodiments of the invention, the carrier will comprise an admixture of a substantially pure, solid form of phosphatidylcholine, for example, Phospholipon 90G (Lipoid GmbH) and a solubilized, liquid form of phosphatidylcholine, for example, Phosal 53 MCT (Lipoid GmbH) to create a moldable admixed carrier. The admixture contains 10% to 50%, preferably about 20% to about 40%, of the solid form of phosphatidylcholine, by weight of the admixture, and 50% to 90%, preferably, about 60% to about 80%, of the liquid form of phosphatidylcholine, by weight of the admixture. More preferably, the admixture contains about 35% the solid form of phosphatidylcholine, based on the weight of the admixture, and about 65% of the liquid form of phosphatidylcholine, by weight of the admixture.

It may be desired, in certain uses of the putties of the invention, that the putty be softer and extrudable. The softer form can be used in minimally invasive surgery (MIS) and injected directly into the implantation site. Softer forms of the putties of the invention can be created by, for example, increasing the amount of the liquid form of the phosphatidylcholine present in the admixture. Such admixtures can include about 25% of the solid form of the phosphatidylcholine, by weight of the admixture and about 75% of the liquid form of the phosphatidylcholine, by weight of the admixture.

The bioactive putties of the invention can then formed by incorporating 60% to 90%, preferably 70% to 80%, of the substantially spherical bioactive particles of the invention, by weight of the putty composition, and 10% to 40%, preferably 15% to 35% or 15% to 25%, of the carrier admixture, by weight of the putty composition. Preferably, the putty compositions contain about 80% of the substantially spherical bioactive glass particles, by weight of the putty composition, and about 20% of the carrier admixture, by weight of the putty composition. Another preferred embodiment includes putty compositions containing about 75% of the substantially spherical bioactive glass particles, by weight of the putty composition, and about 25% of the carrier admixture, by weight of the putty composition.

The putties of the invention can include a unimodal, bimodal, or multimodal particle size distribution of substantially spherical bioactive glass particles.

The putty compositions of the invention have excellent handling properties and are not affected by sterilization. They are moldable and hold their shape without sticking to surgical gloves. The carrier admixtures used in the putty compositions have a short resorption period, do not interfere with bone growth, and are resistant to irrigation.

Stiffer versions of the putty compositions of the invention can be made to create flexible putty strips. Such strips can be used, for example, in vertebral fusions. This is accomplished by increasing the amount of the substantially pure, solid form of phosphatidylcholine in the carrier admixture. Such carrier admixtures can include 50% to 80%, preferably about 60% to about 70%, of the solid form of phosphatidylcholine, by weight of the carrier admixture, and 20% to 50%, preferably about 30% to about 40%, of the liquid form of phosphatidylcholine, by weight of the carrier admixture. For example, flexible putty strips can be prepared using an admixture comprising about 60% of the solid form of phosphatidylcholine, by weight of the admixture, and about 40% of the liquid form of phosphatidylcholine, by weight of the admixture.

Such putty strips can include 60% to 90%, preferably 70% to 80%, of the substantially spherical bioactive particles of the invention, by weight of the putty strip, and 10% to 40%, preferably 15% to 35% or 15% to 25% or 20% to 30%, of the carrier admixture, by weight of the putty strip. Preferably, the putty strips contain about 80% of the substantially spherical bioactive glass particles, by weight of the putty strips, and about 20% of the carrier admixture, by weight of the putty strips. Another preferred embodiment includes putty strips containing about 75% of the substantially spherical bioactive glass particles, by weight of the putty strip, and about 25% of the carrier admixture, by weight of the putty strip.

The putty strips of the invention can include a unimodal, bimodal, or multimodal particle size distribution of substantially spherical bioactive glass particles.

Putty compositions and putty strips of the invention can also be formed using the mechanically-stabilized, HCA-coated bioactive glass particles described herein.

In another embodiment of the invention, the carrier can comprise resorbable or non-resorbable materials that are mixed at the time of surgery and harden into a rigid bone cement material. This includes, but is not limited to, resorbable cements including calcium sulfate, calcium phosphate, calcium carbonate, and non-resorbable cements such as methacrylate-based cements and glass ionomer cements. In this embodiment, the substantially spherical bioactive glass particles of the invention are pre-mixed with dry cement materials. During surgery, a cement-setting solution is mixed into the dry material and the implant changes from a paste to a doughy putty which eventually hardens into a rigid form. These bioactive cements can be used for surgical indications such as fracture repair, bone void filling, fusion, vertebroplasty, kyphoplasty, reconstructive bone repair, and joint replacement.

In one example, the substantially spherical bioactive glass particles of the invention are mixed with a resorbable cement such as calcium sulfate hemihydrate, for example. The bioactive glass/calcium sulfate hemihydrate mixture is then mixed with sterile saline during surgery. As the calcium sulfate hemihydrate reacts with the water to form calcium sulfate dihydrate, the cement thickens into a putty. The cement putty is then placed at the bone defect where it eventually hardens. The resulting rigid implant of calcium sulfate dihydrate and embedded bioactive glass spheres provides mechanical stability to the bone graft site. Once implanted, the implant absorbs body fluid and the bioactive glass dissolution begins. Additionally, the calcium sulfate dihydrate also begins to resorb and slowly exposes the bioactive glass spheres at the surface of the implant. During the resorption process, the implant is replaced by new bone. The use of substantially spherical bioactive glass in a resorbable cement is advantageous since the bioactive glass ions can diffuse out of the cement to stimulate healing on the implant surface.

In an exemplary cement embodiment of the invention, the bioactive cement will comprise an admixture of calcium sulfate hemihydrate (Sigma Aldrich, St. Louis, Mo.) and substantially spherical bioactive glass particles of the invention. The admixture contains 20% to 90%, preferably about 50% to about 80%, of calcium sulfate hemihydrate, by weight of the admixture, and 10% to 80%, preferably, about 20% to about 50%, of the substantially spherical bioactive glass particles, by weight of the admixture. More preferably, the admixture contains about 70% calcium sulfate hemihydrate, based on the weight of the admixture and about 30% of substantially spherical bioactive glass, by weight of the admixture.

The calcium sulfate hemihydrate/bioactive glass mixture will be provided in a kit form with a separate container for the setting solution. At the time of surgery, the setting solution will be combined with the dry calcium sulfate hemihydrate/bioactive glass admixture. The kit contains 1 cc of setting solution for every 2 g to 6 g, preferably 3 g to 4 g, of dry cement material. More preferably, the mixture contains 1 cc of setting solution per 3.5 g of dry cement. Setting solutions are known in the art and may be selected from water, saline, or hydrogel solutions such as gelatin, alginate, chitosan, hyaluronic acid.

Another exemplary embodiment of the present invention comprises compositions including the substantially spherical bioactive glass particles of the invention and a carrier that is a porous, resorbable material. "Porous" materials, as used herein, are materials with an interconnected pore system that connects the outer surface of the material to the interior. Such porous materials allow for in-growth of bone tissue throughout the structure. "Resorbable" materials are those which can be broken down and assimilated or excreted from the mammalian body. Resorbable materials used to create porous bone grafts are known in the art and include, for example, type I collagen, chitosan, alginate, gelatin, hyaluronic acid, and resorbable polymers and copolymers such as poly (hydroxy acids), or a combination thereof.

The substantially spherical bioactive glass particles can be incorporated in the porous, resorbable material to form a sheet using methods known in the art. In those methods employing type I collagen as the carrier, standard collagen processing methods can be used to form the sheets. For example, an acidic slurry of type I collagen fibers and bioactive glass particles of the invention can be cast into a sheet form, neutralized, and freeze-dried to remove all water and create a composition having an interconnected porosity. The resulting sheet can be cross-linked using standard collagen cross-linking methods such as dehydrothermal cross-linking.

The sheets of the invention will contain embedded bioactive glass particles of the invention in a porous collagen network. In addition to collagen, other porous materials can be used to create the sheets, for example, polymer or glass fibers, foams, or meshes.

In one embodiment, a sheet of the invention will comprise 50-90% of the substantially spherical bioactive glass particles of the invention, based on the weight of the sheet, and 10% to 50% of the porous, resorbable material, based on the weight of the sheet. In other embodiments, the sheets contain 80-90% of the substantially spherical bioactive glass particles of the invention, based on the weight of the sheet, and 10% to 20% or the porous, resorbable material, based on the weight of the sheet. The sheets of the invention can be fabricated with a range in density including those from 0.2 g/cc to 0.5 g/cc.

Sheets of the invention can also be formed using the mechanically-stabilized, HCA-coated bioactive glass particles described herein.

Another embodiment of the present invention includes porous, shaped structures comprising sintered, substantially spherical bioactive glass particles. In such embodiments, porous, sintered bioactive glass implants can be created by pouring loose substantially spherical particles into a mold and heating the mold to the bioactive glass sintering point. Unimodal, bimodal, and multimodal particle size distributions can be used within this embodiment of the invention.

In these embodiments, since the glass is sintered and not melted, heating will thermally bind the spheres together at their contact points without causing the structure to collapse. The resulting structure will have an interconnected porosity that is created by the 3-D packing of the spheres together. This method can be used to create a variety of porous shapes including plugs, blocks, wedges, rings, etc. These shapes can be used for foot and ankle fusion, facet fusion, interbody fusion, joint reconstruction, fracture repair, osteotomies, and other surgical procedures. Additionally, the sintered implant can also be immersed in simulated body fluid to result in the formation of an HCA layer. Since the internal porosity is protected from the outer surface, the coating may or may not need to be stabilized with an outer coating, for example, gelatin or hyaluronic acid.

EXAMPLE 1

Putty compositions comprising 45S5 bioactive glass particles of the invention were prepared according to Table I and compared against a commercially available 45S5 bioactive glass putty having irregularly-shaped particles.

TABLE I

| Group | Particle Size Range | Carrier |
|---|---|---|
| 1 | 90-180 μm | Phospholipon 90G and Phosal 53 MCT |
| 2 | 180-355 μm | Phospholipon 90G and Phosal 53 MCT |
| 3 | 355-500 μm | Phospholipon 90G and Phosal 53 MCT |
| 4 | 10% 90-180 μm 90% 355-500 μm | Phospholipon 90G and Phosal 53 MCT |
| 5 | 50% 180-355 μm 50% 355-500 μm | Phospholipon 90G and Phosal 53 MCT |
| 6 | 32-710 μm | Polyethylene glycol and glycerol |

In each group, the carrier was removed from the putties to isolate the particles. Isolated particles were incubated in an SBF dissolution fluid at 37° C. The silica ionconcentration in the dissolution fluid was measured by inductively coupled plasma optical emission spectroscopy.

Figure 8A:
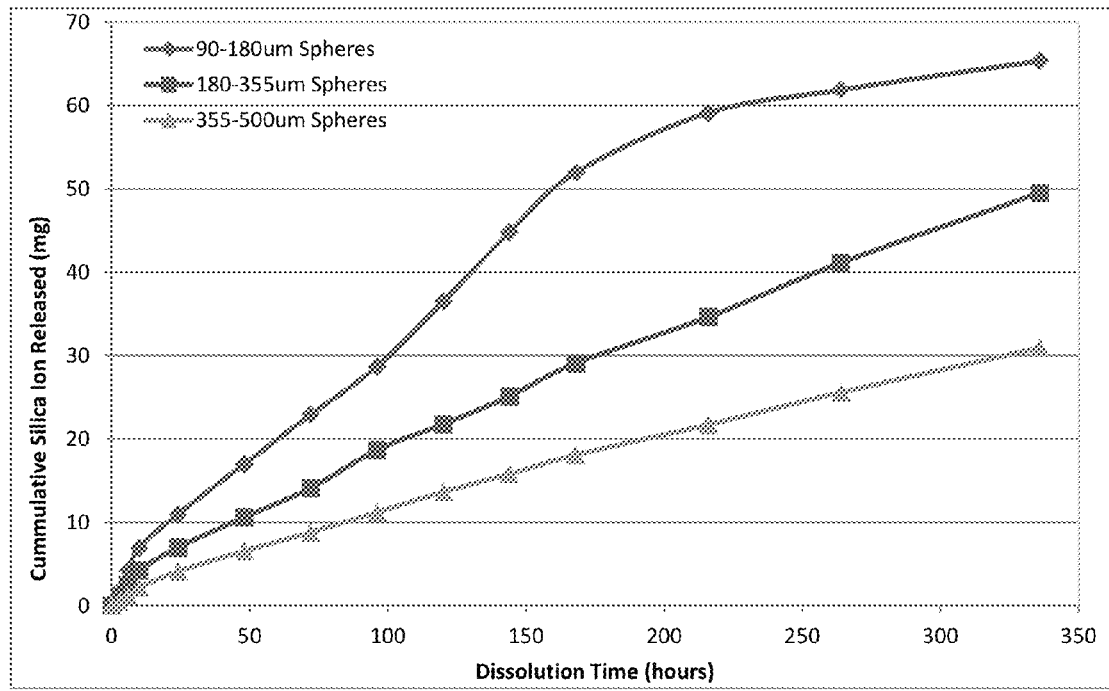
FIG. 8A depicts the silica ion release profiles for various unimodal spherical size ranges (90-180 µm, 180-355 µm, and 355-500 µm substantially spherical particles) showing the benefits of certain embodiments of the invention.
Figure 8B:
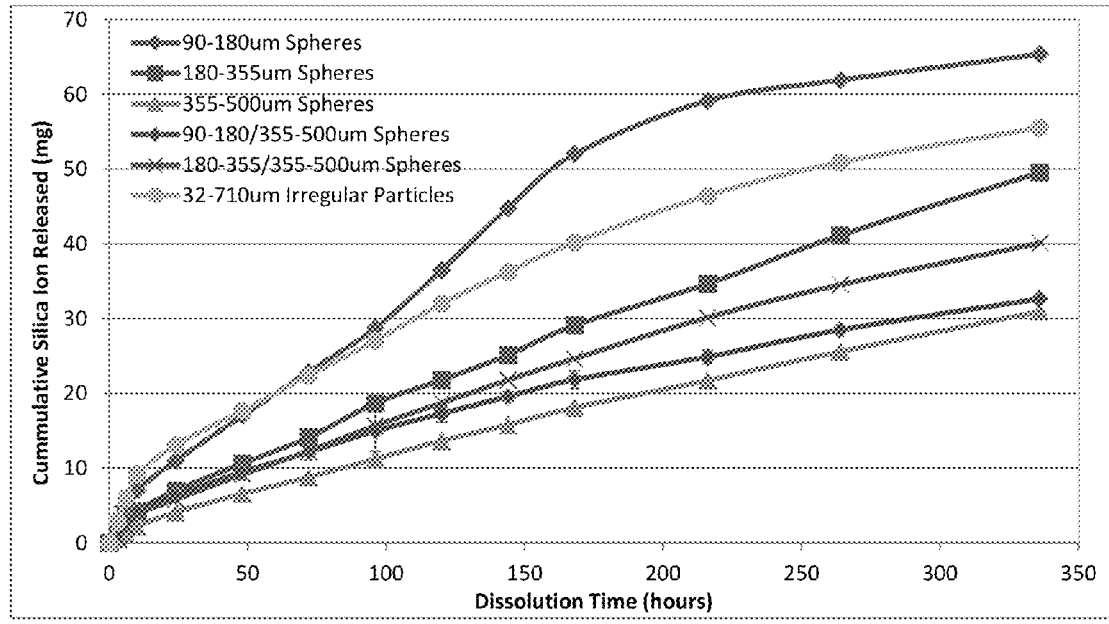
FIG. 8B depicts silica ion release profiles from substantially spherical groups having a bimodal particle size distribution (90-180/355-500 µm; and 180-355 µm/355-500 µm) and the irregular particle group (32-710 µm) of the prior art.

The results of the dissolutions study are shown in FIGS. 8A and 8B. The silica release profiles for the unimodal sphere sizes used in the study (90-180 μm, 180-355 μm, and 355-500 μm) are shown in FIG. 8A. The data showed that the silica release rate (and resultant 45S5 dissolution) was dependent on particle size. The 90-180 μm group demonstrated the fastest release, followed by the 180-355 μm group, and the 355-500 μm group.

The inclusion of the silica release profiles from the bimodal spherical groups (90-180/355-500 μm spheres; and 180-355 μm/355-500 μm spheres) and the 32-710 μm irregular particle group from the prior art is shown in FIG. 8B. The data showed that using a bimodal size distribution allowed the release rate to be controlled. In the spherical bimodal groups, the addition of 90-180 μm and 180-355 μm substantially spherical particles to the 355-500 μm substantially spherical particles increased the silica release rate of the 355-500 μm particles alone. Both spherical bimodal groups had release profiles in between the 180-355 μm group and the 355-500 μm spherical group.

The data also showed that the particle shape has a significant effect on dissolution as seen by the release profile of the 32-710 μm irregular particle group in FIG. 8B. Although this group had particles larger than the largest substantially-spherical group (355-500 μm), the 32-710 μm irregular particle group had a fast release rate that was comparable to the smallest substantially spherical group (90-180 μm). While not wishing to be bound by any particular theory, this effect can be attributed to the quick dissolution of the small, irregular particles and the dissolution of the rough edges on the larger irregular particles.

EXAMPLE 2

Sterile putties were manufactured with 90-180 μm and 355-500 μm 45S5 substantially spherical bioactive glass particles, Phospholipon 90G, and Phosal 53 MCT, and were tested to determine the putty properties. Carrier dissolution was determined by incubating the putty in saline at 37° C. for 7 days and measuring carrier weight loss. In addition, the putty's handling and resistance to irrigation were measured following exposure to hot and cold temperature extremes for 2 weeks (60° C. and −2° C.). Data was compared to a room temperature control. This was done to mimic extreme conditions that may be encountered during product distribution.

The results of the carrier dissolution study showed that the carrier was effectively removed through an aqueous dissolution process. This was represented by a linear decrease in weight during the study. With a total dissolution time of ~5 days, the carrier will be quickly removed from the site and will not interfere with the bone healing process.

The temperature study showed that the handling of the putties exposed to the various storage conditions was identical and there were no differences in moldability, cohesiveness, or stickiness. All putties were easily moldable, maintained their shape, and did not crumble or stick to surgical gloves. In the irrigation study, putties were fully submersed in saline and dissolution was qualitatively assessed over 60 minutes. During the course of the study, the putties exhibited negligible dissolution and remained completely intact with no particles falling off the putty specimen. This was seen for all three storage conditions. The ability of the putty to resist initial dissolution from irrigation is a beneficial property of the carrier and will minimize graft migration due to excessive irrigation. Based on the observations, the putty consistency and resistance to irrigation will aid the surgeon in the placement of the bioactive particles and will allow the graft to stay in place.

EXAMPLE 3

Bioactive glass-containing putties (5 implants per group) were placed in a 6×10 mm critical size defect in the distal femur of New Zealand white rabbits. At 6 and 12 weeks, femurs were harvested, and visualized using x-ray and micro-computed tomography (micro-CT) imaging. Femurs were then embedded in polymethylmethacrylate and serial sections were taken. Histological sections were stained with methylene blue and fuchsin to visualize the implant and the bone. Histology slides were qualitatively assessed to examine the local tissue response to the implant and bioactivity of the bioactive glass particles. Histomorphometric analysis was conducted to quantify the amount of bone in each group. Using image analysis software to identify and quantify the amount of bone in the defect site, average bone formation values for each group were calculated.

The results showed putties using the substantially spherical bioactive glass particles of the invention had the best healing and showed a considerable improvement in bone formation, as compared to the irregular 45S5 particles. A representative 6 and 12 week microCT image for each of the groups is shown in FIG. 9. At 6 weeks, images from the 32-710 μm irregular particle size group showed bone growth from the periphery of the defect towards the center. At the edge of the defect, bone was seen growing on the surface of the particles an in the space between the particles. Bone healing did not span the entire defect, however, and a void filled with intact bioactive glass granules was seen in the center of the defect. By comparison, the 6 week images of the substantially spherical particles of the invention showed substantially more bone growth at the defect site. The best bone formation was seen in the 180-355 μm group, 355-500 μm group, and bimodal groups. These groups showed extensive bone formation throughout the implant area with the entire defect filled in with bone. The 90-180 μm size range of the invention, however, did not have bone throughout the defect. Although there was more bone than the 32-710 μm irregular particle group, there was still a small void in the center of the defect.

By 12 weeks, microCT results showed continued bone formation within the defect in all groups. The 32-710 μm irregular particle group showed bridging bone across the outer cortex, however, there were still some particles without bone growth present in the center of the defect. The 90-180 μm group showed filling of the internal defect with a small gap near the outer cortex. Similar to the 6 week results, the 180-355 μm group, the 355-500 μm group, and the two bimodal groups showed the most bone formation with bone spanning across the entire defect.

The histological analysis of the specimens showed that all groups supported bone growth on the surface and in between the bioactive glass particles. Additionally, the histology showed that all groups were bioactive with the formation of an HCA layer on the particle surface. Qualitatively, the histological analysis matched the microCT data with more bone seen in the 180 μm-355 μm group, the 355 μm-500 μm group, and the two bimodal groups, as compared to the 32-710 μm irregular particle group and the 90-180 μm substantially spherical group.

Figure 10:
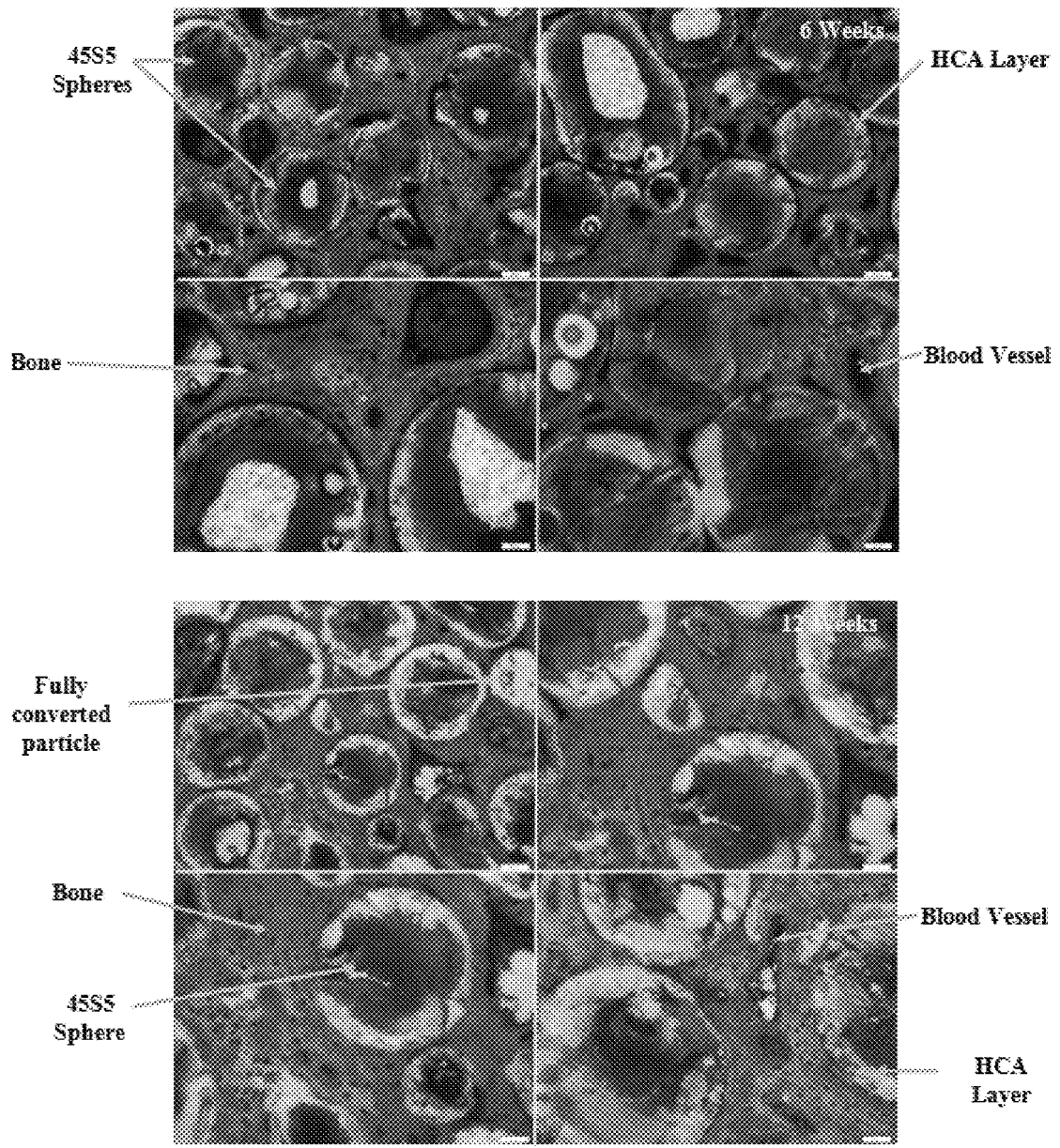
FIG. 10 depicts 6 and 12 week histology results from a rabbit femur study using bimodal 45S5 particles of the invention.

A representative example of the histology is shown in FIG. 10. This image shows bone growth on the surface of the spheres from the 90-180 μm/355-500 μm group at 6 and 12 weeks. As seen from the images, vascularized bone is visible completely surrounding the substantially spherical particles. In addition, the characteristic HCA region is shown as a white layer on the outer surface of the particles. By 12 weeks, bone formation has increased and the HCA layer thickness has increased with some of the smaller particles showing full conversion.

Figure 11:
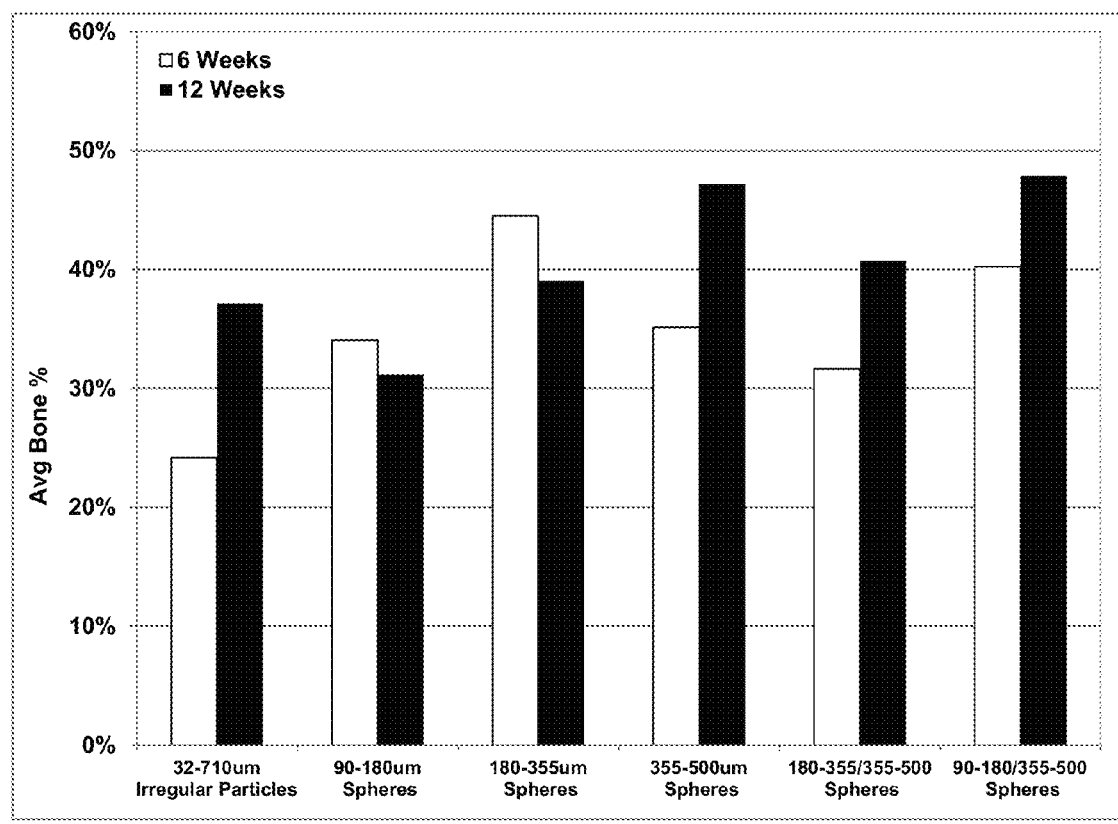
FIG. 11 depicts histomorphometric analysis results from the rabbit femur study comparing particles of the invention to the irregular particle groups of the prior art.

Using the histology images, the amount of bone within the defect of each group was quantified using histomorphometry. The results of the histomorphometric analysis matched the qualitative observations from the microCT and histology analysis, and are shown in FIG. 11. The data showed that the 180-355 μm group, 355-500 μm, and bimodal groups resulted in a substantial increase to the average amount of bone % found at the site at both 6 and 12 weeks. The one formation data was used to calculate the change in bone formation compared to the 32-710 μm irregular particle group. A summary of the increase in bone formation data is shown in Table II.

TABLE II

| Spherical Particle Group | Particle Distribution Type | 6 week increase | 12 week increase (decrease) |
|---|---|---|---|
| 90-180 μm | unimodal | 41% | −16% |
| 180-355 μm | unimodal | 84% | 5% |
| 355-500 μm | unimodal | 45% | 27% |
| 90-180/355-500 μm | bimodal | 66% | 29% |
| 180-355/355-500 μm | bimodal | 31% | 10% |

The data showed that all of the substantially spherical groups (with the exception of 90-180 μm) showed increased bone formation at both timepoints. It was evident from the results that the improved bioactive glass particle shape resulted in faster and more robust bone healing throughout the study. The data also showed that healing response was also dependent on particle size. Comparison within the substantially spherical groups showed that the bimodal group with 10% of the 90-180 nm substantially spherical particles and 90% of the 355-500 nm substantially spherical particles had the best combined 6 and 12-week results.

Conversely, the 90-180 nm group had the lowest bone formation response within the substantially spherical particle groups. This group had an ion release profile (from example 1) similar to the to the 32-710 90-180 nm irregular particle group. Overall, the data showed that control over ion release through particle shape and size can have a substantial improvement on bone healing. Contrary to the prior art, this effect was not dependent on a irregular particle shape with a rough surface but rather a smooth, substantially spherical particle that provided and optimal porosity and ion release profile.

EXAMPLE 3

The substantially spherical 45S5 particles of the invention, or irregularly-shaped 45S5 particles known in the art, can be pre-treated with simulated body fluid to form an HCA-coating on the surface. Simulated body fluid (SBF) is an artificial solution containing ions similar to human extracellular fluid. SBF solutions are well known to those skilled in the art and may have a variety of different compositions. In one embodiment, bioactive glass is incubated at 37° C. in the solution described by Kukubo [Kokubo et al. *J. Biomed. Mater. Res.* 24:721-734 (1990)] for 7 days. Following the formation of the HCA layer, the glass is gently removed from the SBF solution and rinsed.

The resulting HCA-coated particles can then be dip coated using, for example, a 3% solution of hyaluronic acid. Gelatin can also be used as the outer coating. The outer-coated bioactive glass is then allowed to dry to create a mechanically-stabilized, pre-reacted bioactive glass form.

While the above describes the exemplary embodiments, various other modifications and additions will be apparent to those of skill in the art.

REFERENCES

U.S. Pat. No. 4,851,046
U.S. Pat. No. 5,204,106
U.S. Pat. No. 5,658,332
U.S. Pat. No. 6,228,386
Hench et al. "Bonding mechanism at the Interface of Ceramic Prosthetic materials." J. Biomed. Mater. Res. Symp. 117-141 (1971)
Oonishi et al. "Particulate 45S5 compared with hydroxyapatite as a bone graft substitute." Clin. Orthop. Rel. Res. 334: 316-325 (1997)
Xynos et al. "Ionic products of bioactive glass dissolution increase proliferation of human osteoblasts and induce insulin-like growth factor II mRNA expression and protein synthesis." Biochem. Biophys. Res. Commun 276: 461-465 (2000).
Bosetti et al. "The effect of bioactive glasses on bone marrow stromal cell differentiation." Biomaterials 26: 3873-3879 (2005).
Jell et al. "Gene activation by bioactive glasses." J. Mater. Sci: Mater. Med. 17:997-1002 (2006)
Hollis et al. "Factors affecting bone in-growth." In Wise et al. Encyclopedic Handbook of Biomaterials and Bioengineering Vol 1. Boca Raton: CRC Press. Pp. 806-807 (1995).
Kokubo et al. "Solutions able to reproduce in vivo surface-structure changes in bioactive glass-ceramic A-W." J. Biomed. Mater. Res. 24:721-734 (1990).

What is claimed:

1. A composition implantable into a mammalian body comprising:
 a physiologically acceptable carrier comprising an admixture of at least two phospholipids, wherein the admixture comprises a solid form of phosphatidylcholine and a liquid form of phosphatidylcholine; and
 a bimodal particle size distribution of substantially spherical bioactive glass particles;
 wherein the bimodal distribution includes particles of between about 90 μm and about 180 μm and particles of between about 355 μm and about 500 μm.

2. The composition of claim 1, comprising 50%-90% of the substantially spherical bioactive glass particles, by weight of the composition.

3. The composition of claim 1, comprising about 70% to 80% of the substantially spherical bioactive glass particles, by weight of the composition.

4. The composition of claim 1, comprising about 80% to 90% of the substantially spherical bioactive glass particles, by weight of the composition.

5. The composition of claim 1, wherein the bioactive glass is 45S5 glass.

6. A composition implantable into a mammalian body comprising:
 a physiologically acceptable carrier comprising an admixture of at least two phospholipids, wherein the admixture comprises a solid form of phosphatidylcholine and a liquid form of phosphatidylcholine; and
 a particle size distribution of substantially spherical bioactive glass particles;
 wherein the distribution includes particles of between about 355 μm and about 500 μm.

7. The composition of claim 6, comprising 50%-90% of the substantially spherical bioactive glass particles, by weight of the composition.

8. The composition of claim 6, comprising about 70% to 80% of the substantially spherical bioactive glass particles, by weight of the composition.

9. The composition of claim 6, comprising about 80% to 90% of the substantially spherical bioactive glass particles, by weight of the composition.

10. The composition of claim 6, wherein the bioactive glass is 45S5 glass.

11. A composition implantable into a mammalian body comprising:
 collagen; and
 a bimodal particle size distribution of substantially spherical bioactive glass particles;
 wherein the bimodal distribution includes particles of between about 90 μm and about 180 μm and particles of between about 355 μm and about 500 μm.

12. The composition of claim 11, wherein the porous, resorbable material is type I collagen.

13. The composition of claim 11, wherein the composition comprises 50%-90% of the substantially spherical bioactive glass particles, by weight of the composition.

14. The composition of claim 11, wherein the composition comprises 80%-90% of the substantially spherical bioactive glass particles, by weight of the composition.

15. Substantially spherical bioactive glass particles having a bimodal particle size distribution including particles of between about 90 μm and about 180 μm and particles of between about 355 μm and about 500 μm, wherein about 10% to 50% of the particles, by weight, are between about 90 μm and about 180 μm.

16. The particles of claim 15, wherein about 10% of the particles, by weight, are between about 90 μm and about 180 μm.

17. The particles of claim 15, wherein the bioactive glass is 45S5 glass.

* * * * *